US00PP11316P

United States Patent [19]

Bartels

[11] Patent Number: Plant 11,316

[45] Date of Patent: Mar. 28, 2000

[54] SOLIDAGO PLANT NAMED 'BARSEVEN'

[75] Inventor: Goos B. H. Bartels, Aalsmeer, Netherlands

[73] Assignee: Bartels Breeding B.V., Aalsmeer, Netherlands

[21] Appl. No.: 09/145,842

[22] Filed: Sep. 3, 1998

[51] Int. Cl.[7] ..... A01H 5/00

[52] U.S. Cl. ..... Plt./263

[58] Field of Search ..... Plt./263

[56] References Cited

U.S. PATENT DOCUMENTS

P.P. 8,710 5/1994 Bartels et al. ..... Plt./263

*Primary Examiner*—Howard J. Locker
*Assistant Examiner*—Kent L. Bell
*Attorney, Agent, or Firm*—C. A. Whealy

[57] ABSTRACT

A distinct cultivar of potted Solidago plant named 'Barseven', characterized by its compact and mounded plant habit; vigorous and freely branching habit; freely flowering; attractive sprays of numerous yellow inflorescences; tolerance to Powdery Mildew; and good post-production longevity.

1 Drawing Sheet

BACKGROUND OF THE INVENTION

The present invention relates to a new and distinct cultivar of potted perennial Solidago plant, botanically known as *Solidago hybrida* and referred to by the cultivar name 'Barseven'. The new variety is being marketed under the name Sweety.

The new Solidago is a product of a planned breeding program conducted by the Inventor in Aalsmeer, The Netherlands. The objective of the breeding program was to create new compact potted Solidagos having uniform plant habit and uniform flowering.

The new Solidago originated from a cross made in 1994 by the Inventor of two propietary Solidago seedling selections. The cultivar 'Barseven' was discovered and selected by the Inventor as a flowering plant within the progeny of the stated cross in a controlled environment in Aalsmeer, The Netherlands. The new Solidago differs from the parent selections in ray floret color, stem length and flowering habit.

Asexual reproduction of the new Solidago by terminal cuttings taken at Aalsmeer, The Netherlands, has shown that the unique features of this new Solidago are stable and reproduced true to type in successive generations of asexual reproduction.

SUMMARY OF THE INVENTION

The following traits have been repeatedly observed and are determined to be the unique characteristics of 'Barseven'. These characteristics in combination distinguish 'Barseven' as a new and distinct cultivar:

1. Compact and mounded plant habit, excellent for pot plant culture.
2. Vigorous and freely branching.
3. Freely flowering.
4. Attractive sprays of numerous yellow inflorescences.
5. Tolerant to Powdery Mildew.
6. Good post-production longevity.

The cultivar Barseven has not been observed under all possible environmental conditions. The phenotype may vary somewhat with variations in environment such as temperature, daylength and light intensity, wihtout, however, any variance in genotype.

BRIEF DESCRIPTION OF THE PHOTOGRAPH

The accompanying colored photograph illustrates the overall apperance of the new Solidago, showing the colors as true as it is reasonably possible to obtain in a colored reproduction of this type. The photograph comprises a side perspective view of a typical flowering plant of the new Solidago. Floret and foliage colors in this photograph may vary from the actual ray floret and foliage colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Aalsmeer, The Netherlands, in a glass-covered greenhouse with average day and night temperatures of 18 and 16° C., respectively. Plants received long day/short night treatments for the first seven weeks, then short day/long night treatments for the next five weeks. Plants were pinched (terminal apices removed) two weeks after planting.

Botanical classification: *Solidago hybrida* cultivar 'Barseven'.

Commercial classification: Potted Solidago.

Parentage:

*Male or pollen parent*.—Proprietary *Solidago hybrida* seedling selection.

*Female or seed parent*.—Proprietary *Solidago hybrida* seedling selection.

Propagation:

*Type*.—Terminal tip cuttings.

*Time to rooting*.—Summer: About 7 days at a temperature of 18° C. Winter: About 10 days at a temperature of 16° C.

*Rooting habit*.—Fine, fibrous and well-branched.

Plant description:

*Appearance*.—Perennial herbaceous decorative container plant. Relatively compact and mounded plant habit; stems upright to outward forming an inverted triangle. Appropriate for 12 to 15-cm. containers. Usually about 12 weeks are required to produce a flowering plant.

*Branching habit*.—Freely branching; pinching enhances branching; typically ten to fifteen lateral branches develop after pinching.

*Growth rate*.—Vigorous.

*Plant height*.—About 40 cm.

*Plant width*.—About 15 cm.

*Lateral branch length*.—About 10 cm.

*Internode length*.—About 1.25 cm.

*Stem texture*.—Slightly pubescent.

*Foliage description*.—Arrangement: Alternate. Quantity of leaves per lateral branch: About 28. Shape: Oblong; apex sharply acute; base attenuate; margin toothed. Length: About 11 cm. Width: About 1 cm. Texture: Rough, slight pubescence on upper surface. Color: Young leaves, upper surface: 139A. Young leaves, lower surface: 137A. Fully expanded leaves, upper surface: 139A. Fully expanded leaves, lower surface: 137A. Venation, upper surface: 139A. Venation, lower surface: 137A.

Flowering description:

*Apperance*.—Numerous spike-like panicles, plume like. Disc and ray florets arranged acropetally on a capitulum.

*Flowering response*.—Under natural conditions, plants flower in the late summer/autumn. At other times of the year, infloresence initiation and development can be induced under short day/long night conditions. Response time is about 10 weeks.

*Post-Production longevity*.—Good, inflorescence last about three weeks on the plant. Inflorescences persistent.

*Quantity of inflorescences*.—Flowering stems may form at every leaf axil. Freely flowering, usually about 500 inflorescences per plant.

*Panicle length*.—About 15 cm.

*Bud*.—Shape: Cylindrical. Length: About 2 mm. Diameter: About 1 mm. Color: 143A.

*Ray florets*.—Number of ray florets per inflorescence. About 12. Shape: Oblong; apex dentate; base attenuate; margin entire. Length: About 2 mm. Width: About 1 mm. Texture: Smooth, glabrous. Color: When opening, upper and lower surfaces: 2B. Mature, upper and lower surfaces: 2B, fading to 2C.

*Disc florets*.—Quantity: About 5 per inflorescence. Length: About 1 mm. Width: About 0.5 mm. Color: 7A.

*Sepals*.—Quantity: About ten. Shape: Oblong, linear; apex sharply pointed; margin entire. Texture: Smooth. Color, upper and lower surfaces: 143A.

*Peduncle*.—Strength: Strong. Length: Apical peduncle: About 3 mm. Fourth peduncle: About 4 mm. Seventh peduncle: About 5 mm. Texture: Slight pubescence. Color: 143A.

*Reproductive organs*.—Androecium: Present on disc florets only. Anther size: Less than 0.5 mm. Anther color: 7A. Pollen: Abundant, 7A in color. Gynoecium: Present on both ray and disc florets. Pistil length: About 0.75 mm. Stigma color: 7A. Style color: 7A.

Disease resistance: Tolerant to Powdery Mildew.

Seed production: Seed production has not been observed.

It is claimed:

1. A new and distinct cultivar of Solidago plant named 'Barseven', as illustrated and described.

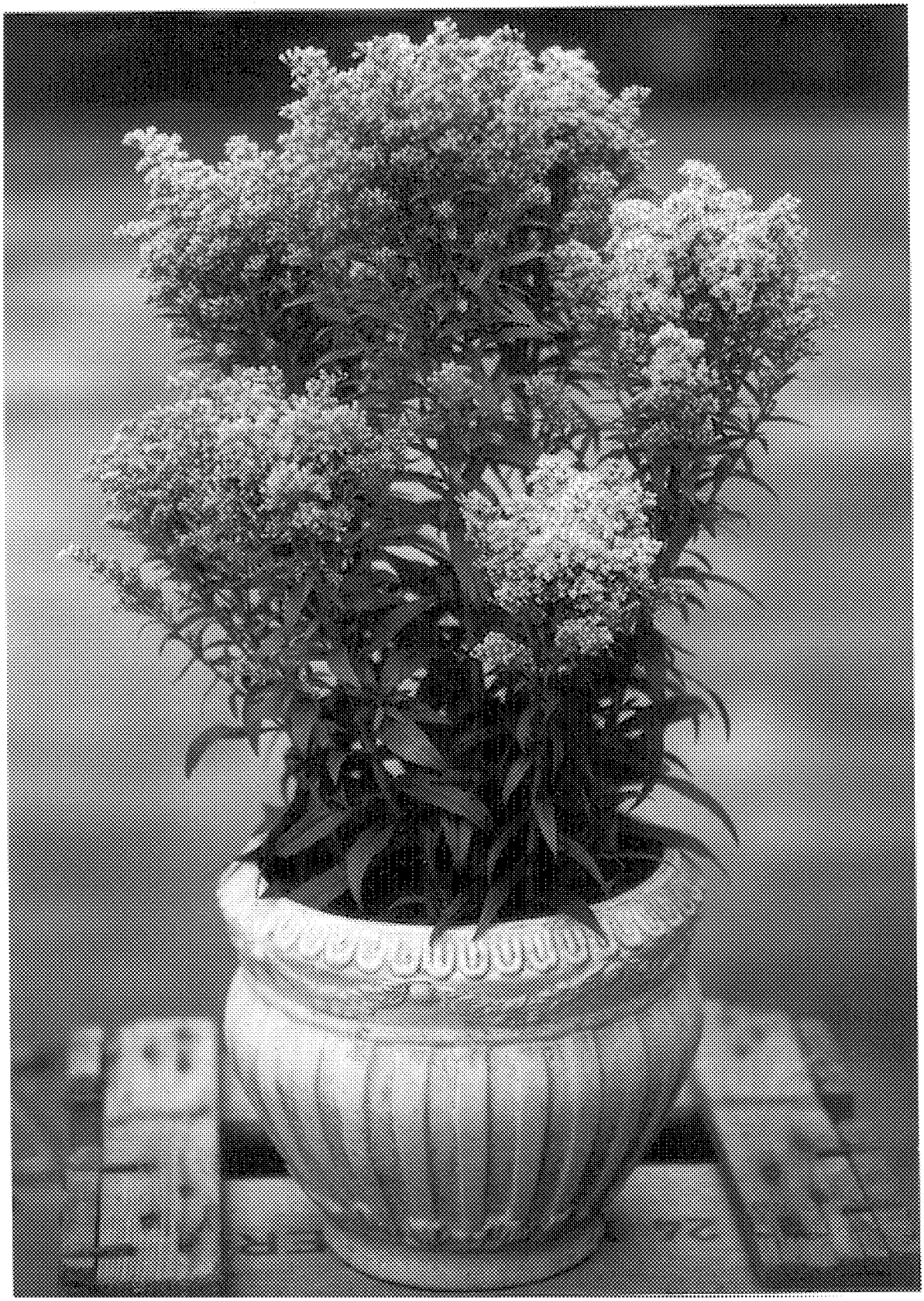

* * * * *